United States Patent [19]

Blume et al.

[11] Patent Number: 4,870,088

[45] Date of Patent: Sep. 26, 1989

[54] 1-[1-ARYL-1-HYDROXY-2-AZOLYL-ETHYL]-1-ARYL-CYCLOPROPANE DERIVATIVES, AND THEIR FUNGICIDAL USE THEREOF

[75] Inventors: Ernst Blume, Kriftel; Wolfgang Schaper, Frankfurt am Main; Heinz Ehrhardt, Rehling; Wolfgang Raether, Dreieich; Walter Dittmar, Hofheim am Taunus; Heinz Hänel, Bad Homburg; Burkhard Sachse, Kelkheim, all of Fed. Rep. of Germany

[73] Assignee: Hoechst Aktiengesellschaft, Frankfurt am Main, Fed. Rep. of Germany

[21] Appl. No.: 25,621

[22] Filed: Mar. 13, 1987

[30] Foreign Application Priority Data

Mar. 15, 1986 [DE] Fed. Rep. of Germany ....... 3608792

[51] Int. Cl.$^4$ .................... A61K 31/44; C07D 401/12
[52] U.S. Cl. ..................... 514/340; 514/341; 514/399; 514/397; 514/383; 514/255; 514/326; 514/274; 514/367; 546/276; 546/278; 546/210; 548/341; 548/335; 548/262; 548/336; 548/202; 548/203; 548/247; 548/179; 544/370; 544/366; 544/318; 544/315; 544/333
[58] Field of Search ................ 546/276, 278; 514/340, 514/341

[56] References Cited

FOREIGN PATENT DOCUMENTS 0180850 5/1986 European Pat. Off. .

*Primary Examiner*—Jane T. Fan
*Attorney, Agent, or Firm*—Finnegan, Henderson, Farabow, Garrett & Dunner

[57] ABSTRACT

Compounds I

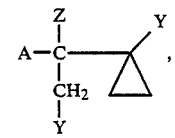

where A equals t-butyl or a large number of (substituted) aromatics; Y equals azolyl; or Y equals —X—R$^1$ where X=oxygen or sulfur and R$^1$ equals (cyclo)alkyl or (heterocyclic) aryl; or Y equals

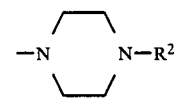

where R$^2$ equals (cyclo)alkyl, acetyl or aryl; or Y equals —NR$^3$R$^4$ where R$^3$/R$^4$ is alkyl; or Y equals several nitrogen-containing heterocyclic rings; Z equals OH, alkylcarbonyloxy, hal, alkoxy or benzyloxy; and the salts thereof are effective antimycotics or fungicides.

They are obtained by reaction of II

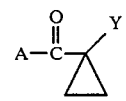

with (CH$_3$)$_2$

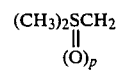

and further reaction of the compound IV

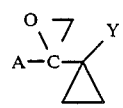

obtained from this with a nucleophile YM (M=hydrogen or a metal equivalent).

The compounds I (where Z=OH) resulting from this can be acylated or alkylated, or converted into I where Z=hal.

7 Claims, No Drawings

1-[1-ARYL-1-HYDROXY-2-AZOLYL-ETHYL]-1-ARYL-CYCLOPROPANE DERIVATIVES, AND THEIR FUNGICIDAL USE THEREOF

The invention relates to 1,1-disubstituted cyclopropane derivatives, processes for the preparation thereof, and pharmaceutical compositions containing such compounds and the use thereof as pharmaceuticals, particularly as antimycotics and plant protection agents, for example as fungicides and growth regulators.

1-Aryl-1-cyclopropyl-2-azolyl-ethanoles are described in Patent Specification DE-A-No. 3,433,553, and bis-triazoles are described in EP-A No. 0,164,246 as antimycotics and fungicides; however, their action and compatibility is not completely satisfactory.

It has now been found that the compounds according to the invention, which essentially differ from the abovementioned compounds through the type of substituents on the cyclopropane ring, has very good antimicrobial properties, particularly antimycotic properties. They are therefore suitable for use for combating fungi in humans and animals. Through the fungicidal and growth-regulating properties, they are also suitable as plant protection agents.

The invention therefore relates to cyclopropane derivatives of the formula (I)

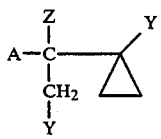

in which:

A denotes t-butyl, phenyl, biphenyl, phenoxyphenyl, benzylphenyl, benzyloxyphenyl, phenylthiophenyl, phenylsulfinylphenyl, phenylsulfonylphenyl, naphthyl, 1,2,3,4,-tetrahydronaphthyl, indanyl, fluorenyl, thienyl, furyl, pyridyl, isoxazolyl, pyrazolyl, benzofuryl, or benzothienyl, where the ring systems mentioned may be unsubstituted or substituted by 1-3 substituents which are identical or different and which are F, Cl, Br, I, $(C_1-C_8)$-alkyl, straight-chain or branched and unsubstituted or substituted by 1-9 F or Cl atoms, $(C_3-C_8)$-cycloalkyl, $(C_1-C_8)$-alkoxy, straight-chain or branched and unsubstituted or substituted by 1-9 F or Cl atoms, $(C_3-C_8)$cycloalkyl-$(C_1-C_4)$alkyl, $(C_1-C_8)$alkylthio, $(C_1-C_8)$-alkylsulfinyl, $(C_1-C_8)$-alkylsulfonyl, $NO_2$ or CN;

Y (1) denotes

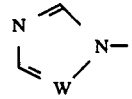

where W=CH or N (2) denotes $-X-R^1$ where X=$-O-$, $-S-$, S=O or $SO_2$, and $R^1$=$(C_1-C_{12})$-alkyl (straight-chain or branched, unsubstituted or substituted by 1 to 3 F, Cl or Br atoms or $CH_3$ groups), $(C_2-C_{20})$-alkenyl (straight-chain or branched; mono- or polyunsaturated, in the form of the pure E or Z isomers or mixtures of E/Z diastereomers, unsubstituted or substituted by 1 to 3 F, Cl or Br atoms or $CH_3O$ groups), $(C_2-C_{20})$-alkynyl (straight-chain or branched; unsubstituted or substituted by 1 to 3 F, Cl or Br atoms or $CH_3O$ groups), $(C_2-C_{20})$alkenynyl (straight-chain or branched; mono- or polyunsaturated, in the form of the pure E or Z isomers or mixtures of E/Z diastereomers, unsubstituted or substituted by 1 to 3 F, Cl or Br atoms or $CH_3O$ groups), $(C_3-C_8)$cycloalkyl, $(C_3-C_8)$cycloalkyl-$(C_1-C_4)$-alkyl, phenyl, biphenylyl, phenoxyphenyl, phenylthiophenyl, phenyl$(C_1-C_4)$-alkyl, naphthyl, biphenylyl-$(C_1-C_4)$-alkyl, phenylthiophenyl(-$C_1-C_4$)-alkyl, phenoxyphenyl$(C_1-C_4)$alkyl, naphthyl$(C_1-C_4)$-alkyl, benzothiazol-2-yl, benzimidazol-2-yl, N-$(C_1-C_4)$-alkylbenzimidazol-2-yl, benzyl, pyridyl, pyrid-2-yl-methyl, pyrid-3-yl-methyl, pyrid-4-yl-methyl, pyrimidin-2-yl, pyrimidin-2-yl-methyl, pyrimidin-4-yl-methyl, pyrimidin-5-yl-methyl, furfuryl, thien-2-yl, thien-3-yl, thien-2-yl-methyl, thien-3-yl-methyl, isoxazol-4-yl-methyl, thiazol-2-yl-methyl, thiazol-5-yl-methyl, thiazol-5-yl-eth-2-yl, $(C_2-C_3)$-alkyl-X-aryl, $(C_2-C_3)$-alkyl-oxyaryl (where X is defined as above and aryl equals phenyl, benzyl, thien-2-yl-methyl or thien-3-yl-methyl), benzothiazol-2-yl-methyl, quinolin-2-yl-methyl or pyridyl phenyl-methyl, where the ring systems mentioned are unsubstituted or substituted by 1, 2 or 3 substituents which are identical or different and in each case denote F, Cl, Br, I, $CF_3$, $(C_1-C_4)$-alkyl or $(C_1-C_4)$-alkoxy; where, however, the ring systems pyrimidinyl and thienyl are unsubstituted or substituted by the above mentioned substituents or by a phenyl which in turn is unsubstituted or substituted as defined above, (3) denotes

where $R^2$=$(C_1-C_8)$-alkyl, $(C_5-C_8)$-cycloalkyl, acetyl, phenyl or benzyl; where the phenyl nucleus is in each case unsubstituted or substituted by 1-3 F, Cl, Br, I, $CF_3$, $(C_1-C_4)$-alkyl or $(C_1-C_4)$-alkoxy groups, (4) denotes

where $R^3$ and $R^4$ are identical or different and denote $(C_1-C_4)$alkyl, or (5) denotes

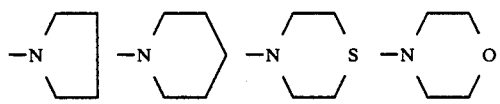

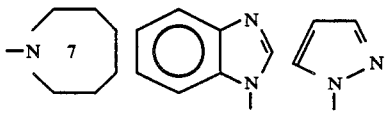

where at least one of the two Y group has the meaning of Y (1); and

Z=OH, (C₁-C₄)-alkylcarbonyloxy, F, Cl, Br, (C₁-C₄)-alkoxy or benzyloxy, unsubstituted or monosubstituted or disubstituted by F, Cl, Br or CF₃;

and the salts thereof with physiologically acceptable acids, with the exception of those compounds in which, simultaneously, (a) both Y have the meaning of Y (1) where W=N, and (b) A has the meaning phenyl, optionally substituted by 1-3 substituents which, independently of one another, are selected from F, Cl, Br, I, CF₃, (C₁-C₄)-alkyl and (C₁14 C₄)-alkoxy, or 5-chloropyrid-2-yl, and (c) Z has the meaning as stated above.

Preferred compounds I are those in which at least one of the substituents has the following meaning:

A: phenyl, biphenyl, 1,2,3,4-tetrahydronaphthyl, thienyl or indanyl, in each case unsubstituted or substituted in the aromatic ring by one or two substituents which are identical or different and in each case denote F, Cl, Br, CF₃, (C₁-C₄)-alkyl or (C₁-C₄)-alkoxy,

Y: (1)

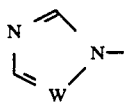

where W=CH or N (2) —X—R¹, where

X=O or S, and

R¹=(C₁-C₁₅)-alkyl, straight-chain or branched, (C₂-C₁₅)-alkenyl, straight-chain or branched and mono- or polyunsaturated, phenyl, biphenylyl, phenoxyphenyl, phenylthiophenyl, phenyl-(C₁-C₂)alkyl, naphthyl, biphenylyl(C₁-C₂)alkyl, naphthyl(C₁-C₂)alkyl, benzothiazol-2-yl, benzimidazol-2-yl, furfuryl, thien-2-yl-methyl, thien-3-yl-methyl, isoxazol-4-yl-methyl, pyrid-3-yl-methyl, pyrid-4-yl-methyl, ethyl-thio-aryl, where aryl equals phenyl, benzyl, thien-2-yl-methyl or thien-3-yl-methyl, where the ring systems mentioned are unsubstituted or substituted by 1, 2 or 3 substituents which are identical or different and in each case denote F, Cl, Br, CF₃, methyl or methoxy groups, (3)

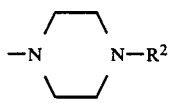

where

R²=phenyl or benzyl, in each case unsubstituted or substituted by 1 or 2 F, Cl, Br, CF₃, methyl or methoxy groups, Z=OH, OCH₃, F or Cl where at least one of the two Y groups has the meaning of Y (1), and the salts thereof with physiologically acceptable acids.

Very particularly preferred compounds I are those in which at least one of the substituents has the following meaning:

A Phenyl or thienyl, in each case unsubstituted or substituted by 1 or 2 F or Cl atoms, methyl or methoxy

Y(1)

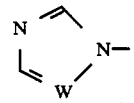

where W=CH or N (2) —X—R¹ where

X=O or S, and

R¹=(C₁-C₁₂)-alkyl (straight-chain or branched), geranyl, neryl, phenyl, benzyl, naphthyl, thien--2yl-methyl, thien-3-yl-methyl, isoxazol-4-yl-methyl, pyrid-3-yl-methyl or pyrid-4-yl-methyl, in each case unsubstituted, or monosubstituted or disubstituted by F, Cl, methyl or methoxy Z=OH where at least one of the two Y groups has the meaning of Y (1), and the salts thereof with physiologically acceptable acids.

The (C₁-C₁₂)-alkyl or (C₁-C₄)-alkyl groups which occur as substituents or occur in connection with other substituents may be unbranched or branched and denote, for example, the methyl, ethyl, propyl, 1-methylethyl, butyl, 2-methylpropyl, 1,1-dimethylethyl, pentyl, hexyl, heptyl, octyl, nonyl, decyl, undecyl or dodecyl group; the fluorine-substituted or chlorine-substituted alkyl groups may denote, for example, the trifluoromethyl, trichloromethyl, 1,1,2,2-tetrafluoroethyl or the nonafluorobutyl group; the (C₃-C₈)-cycloalkyl groups may denote the cyclopropyl, cyclobutyl, cyclopentyl, cyclohexyl, cycloheptyl or cyclooctyl group; and the (C₃-C₈)-cycloalkyl-(C₁-C₄)alkyl groups may denote, for example, the cyclopropylmethyl, cyclopentylmethyl, cclohexylmethyl, cyclohexylethyl, cycloheptylmethyl or cyclooctylmethyl group.

The present invention relates to the compounds (I) in the form of the free base or in the form of an acid-addition salt or in the form of a physiologically hydrolyzable and acceptable derivative.

Examples of pharmaceutically acceptable salt-forming acids are inorganic acids, such as hydrochloric acid, hydrobromic acid, hydroiodic acid, sulfuric acid, phosphoric acid or nitric acid, or organic acids, such as malonic acid, oxalic acid, gluconic acid, camphorsulfonic acid, benzenesulfonic acid, acetic acid, propionic acid or p-toluenesulfonic acid.

Suitable physiologically hydrolyzable and acceptable derivatives are, for example, derivatives which are esterified at the hydroxyl group and which can be hydrolyzed under physiological conditions to form the free acids, which themselves are again physiologically acceptable, i.e. are nontoxic at the doses necessary.

The compounds (1) have at least one asymmetrical carbon atom and can thus occur as enantiomers and diastereomers. The invention covers the pure isomers and the mixtures thereof. The mixtures of diastereomers may be separated into the components by customary methods, for example by selective crystallization from suitable solvents or by chromatography on silica gel or alumina. Racemates can be separated into the enantiomers by conventional methods, thus, for example, by salt formation with an optically active acid, separation of the diastereomeric salts and liberation of the pure enantiomers using a base.

The invention furthermore relates to a process for the preparation of compounds of the formula (I), wherein a compound of the formula (II)

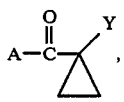

in which A and Y have the meanings mentioned in claim 1, is reacted with a sulfur ylide of the formula III,

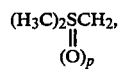

in which p denotes zero or 1 to form a compound of the formula IV

and the compound IV is subsequently reacted with a nucleophile of the formula Y-M, in which
Y has the meanings mentioned in claim 1, and
M is hydrogen or a metal equivalent,
a compound I having Z=OH being produced, and, if desired, this compound I is acylated or alkylated and, if appropriate, oxidized on the sulfur of a thioether group to form the sulfoxide or sulfone,
and, if appropriate, the compound I having Z=OH is converted into a compound having Z=F, Cl or bromine, and a compound of the formula (I) thus obtained is isolated in the form of the free base or in the form of an acid-addition salt.

For the preparation of the compounds of the formula (I), a ketone of the formula (II), in which A and Y have the abovementioned meanings, is reacted, in a first reaction stage for the preparation of the compounds of the formula (IV), with a sulfur ylide of the formula (III) in an inert solvent, preferably dimethyl sulfoxide, or in mixtures of dimethyl sulfoxide with other inert solvents, for example tetrahydrofuran. A temperature range between −10° and 50° C., preferably between 0° and 30° C., is expedient here when a sulfur ylide of the formula (III) in which p is 0 is used; a temperature range between 0° and 80°, preferably between 20° and 60°, is expedient when a sulfur ylide of the formula (III) in which p is 1 is used.

The intermediates of the formula IV are converted into the final product of the formula I, where Z=OH, in a second reaction stage by reaction with a compound of the formula Y-M, in which Y and M have the abovementioned meanings.

The abovementioned reaction is carried out in a temperature range of 20°–160° C., if appropriate in an inert solvent, if appropriate in the presence of a base.

Suitable solvents are, for example, N,N-dimethylformamide, N,N-dimethylacetamide, dimethyl sulfoxide, sulfolane, N-methyl-2-pyrrolidone, dioxane, tetrahydrofuran, acetonitrile, 4-methyl-2-pentanone, methanol, ethanol, isopropyl alcohol, propanol, butanol, pentanol, tert.-butyl alcohol, methyl glycol, glacial acetic acid, methylene chloride or an aromatic hydrocarbon, such as benzene, chlorobenzene, nitrobenzene, toluene or xylene, or water. Mixtures of the solvents mentioned as examples may also be used.

Suitable bases are, for example, alkali metal or alkaline earth metal carbonates, hydrogen carbonates, hydroxides, alcoholates or hydrides, such as, for example, sodium carbonate, sodium hydrogen carbonate, potassium carbonate, sodium hydroxide, sodium methylate or sodium hydride, or organic bases, for example tertiary amines, such as triethylamine, tributylamine, ethylmorpholine or pyridine, dimethylaminopyridine, quinoline or 1,5-diazabicyclo[5,4,0]-undec-5-ene(1,8,7) (DBU), 1H-imidazole or 1H-1,2,4-triazole.

The reaction of the compounds of the formula II with the compounds of the formula III to form the intermediates of the formula IV, and the reaction of these with compounds of the formula Y-M to form compounds of the formula I where Z=OH may also be carried out as a one-pot process.

To this purpose, a solution of a compound of the formula IV in one of the abovementioned inert solvents is initially prepared, as stated above, by reaction of a compound of the formula II with a compound of the formula III. An at least equivalent amount of a compound of the formula Y-M, and, if appropriate, a catalytic or equivalent amount of one of the abovementioned bases is subsequently added to this solution, and the further procedure as mentioned above s carried out.

Compounds of the formula I in which Z denotes $(C_1-C_4)$-alkoxy or benzyloxy, unsubstituted, or monosubstituted or disubstituted by F, Cl, Br or $CF_3$, are prepared by reacting a compound of the formula I where Z=OH with an appropriate alkyl halide or benzyl halide, preferably a chloride or bromide, in the presence of a base, in an inert solvent, in a temperature range of 0°–100° C. Those solvents and bases are preferably used which are mentioned for the reaction of compounds of the formula IV with Y-M.

Compounds of the formula I in which Z denotes $(C_1-C_4)$-alkylcarbonyloxy are prepared by reacting a compound of the formula I where Z=OH with an appropriate alkyl carbonyl halide, preferably an alkyl carbonyl chloride, or alkylcarboxylic anhydride, in the presence of a base, in an inert solvent, in a temperature range from −10° to 120° C.

Those solvents and bases are preferably used which are specified for the reaction of compounds of the formula IV with Y-M.

Compounds of the formula I in which Z denotes F, Cl or bromine are prepared by reacting a compound of the formula I where Z=OH with thionyl chloride, thionyl bromide, sulfur tetrafluoride or diethylaminosulfur trifluoride ($Et_2NSF_3$), in an inert solvent, if appropriate in the presence of a base, in a temperature range of 0°–80° C.

Those solvents and bases are preferably used which are specified for the reaction of compounds of the formula IV with Y-M.

Compounds of the formula I which contain a thioether group may be oxidized at the sulfur to form a sulfoxide or sulfone. To accomplish this, such compounds of the formula I are reacted with an oxidant, such as, for example, hydrogen peroxide or m-chloroperbenzoic acid, in an inert solvent, in a temperature range from −10° to 80° C. One mole equivalent of oxidant is added for the preparation of sulfoxides, and two mole equivalents, if appropriate also an excess, for the preparation of sulfones.

Those solvents are preferably used which are specified for the reaction of compounds of the formula IV with Y-M.

Preparation of the starting materials

For the preparation of compounds of the formula II Compounds of the formula II in which A and Y have the meanings specified in claim 1 are preferably prepared by reacting a compound of the formula VI

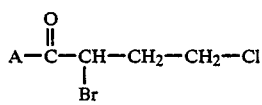
VI in which A has the meanings specified in claim 1, with a compound of the formula Y-M, in which Y and M have the meanings specified in claim 1.

The above reaction is carried out either (a) in one stage, in an inert solvent, in the presence of at least 2 mole equivalents of a base, in a temperature range of 0°–120° C., or (b) in two stages, by initially preparing a compound of the formula VII

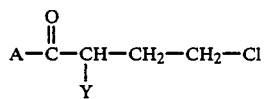
VII in which A and Y have the abovementioned meanings, in an inert solvent, in the presence of at least one mole equivalent of a base, in a temperature range of 0°–50° C.

Those solvents and bases are preferably used, as also in the one-stage version (a), which are specified for the reaction of compounds of the formula IV with Y-M.

In a second reaction step, the compounds of the formula VII, if appropriate after work-up and purification, are converted into compounds of the formula II under the conditions of a phase-transfer reaction. To this purpose, a solution of the compounds of the formula VII in an inert solvent is reacted, with vigorous stirring and in the presence of a phase-transfer catalyst, with a base, preferably a powdered alkali metal hydroxide or alkali metal carbonate, such as, for example, sodium hydroxide, potassium hydroxide, sodium carbonate or potassium carbonate, or a concentrated aqueous solution of the same, preferably in a temperature range of 20°–100° C.

Those solvents are used which are specified for the reaction of compounds of the formula IV with Y-M.

Suitable phase-transfer catalysts are quaternary ammonium or phosphonium salts, crown ethers or polyethylene glycols. Examples of such salts are listed in the monograph by W. P. Weber and G. W. Gockel, Phase Transfer Catalysis in Organic Synthesis, Berlin, Springer Verlag, 1977. Tetrabutylammonium bromides and benzyltriethylammonium chloride have proven particularly suitable for the present purpose.

The two-stage process is particularly advantageous when compounds of the formula II in which A or Y contain a radical which is easily alkylated are prepared.

The compounds of the formula II may also be prepared by reacting a compound of the formula VIII,

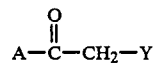
VIII in which A and Y have the abovementioned meanings, with at least one mole equivalent of 1,2-dibromoethane.

The reaction above is preferably carried out in a temperature range of 20°–100° C. under the conditions of a phase-transfer reaction as specified above.

The compounds of the formulae II and VII, the preparation of which is described in the present application, which are used here as starting materials are likewise described in the parallel German Pat. No. (P3,608,727.0, HOE 86/F 059).

Compounds of the formula VI can be prepared from the appropriate ω-chloroketones by reaction of $Br_2$, if appropriate in a solvent, preferably in glacial acetic acid or methylene chloride, in a temperature range of 0°–60° C. The ω-chloroketones necessary are known or can be prepared analogously to this. The starting materials of the formula III, Y-M and VIII are likewise known or can be obtained by known processes.

The invention furthermore relates to a process for the preparation of compounds of the formula I, according to which a compound of the formula II

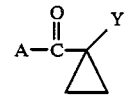
II in which A and Y have the meanings mentioned in claim 1, is reacted with a phosphorus ylide to form a compound of the formula V

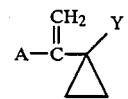
V and the compound V is subsequently reacted with an organic peroxide to form a compound of the formula IV

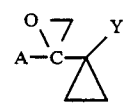
IV and the compound IV is subsequently reacted with a nucleophile of the formula Y-M, in which Y has the meanings mentioned in claim 1, and M is hydrogen or a metal equivalent, a compound I where Z=OH being produced, and, if desired, this compound I is acylated, alkylated or converted into a compound where Z=F, Cl or Br, and, if appropriate, oxidized on the sulfur of a thioether group to form the sulfoxide or sulfone, and, if appropriate, converted into the salt with a physiologically acceptable acid.

For the preparation of the compounds of the formula I, a ketone of the formula II, in which A and Y have the abovementioned meanings, is reacted, in a first reaction step for the preparation of compounds of the formula V, with a phosphorus ylide in an inert solvent, in a temperature range from $-60°$ to $+80°$ C.

The phosphorus ylide used here is prepared by reacting a methyltriarylphosphonium salt, preferably methyltriphenylphosphonium chloride, bromide or iodide, with a strong base in an inert solvent. Suitable bases are, for example, alkali metal or alkaline-earth metal hydrides, amides or alcoholates, sodium bistrimethylsilylamide or organolithium compounds, such as, for example, n-butyllithium or phenyllithium.

Those solvents are used which are specified for the reaction of compounds of the formula IV with Y-M.

In a second reaction step for the preparation of compounds of the formula IV, a compound of the formula V is reacted with an oxidant, in an inert solvent, in a temperature range from $-10°$ to $+80°$ C., if appropriate in the presence of a base, a base and a nitrile, such as, for example, benzonitrile, or thionyl-bisimidazole or thionyl-bistriazole.

Suitable oxidants are, for example, $H_2O_2$ or percarboxylic acids, such as, for example, peracetic acid, trifluoroperacetic acid, perbenzoic acid or m-chloroperbenzoic acid.

Those bases and solvents are used which are specified for the reaction of compounds of the formula IV with Y-M.

In a third reaction step for the preparation of compounds of the formula I where Z=OH from compounds of the formula IV, a procedure is followed as specified in the process above.

If desired, these compounds of the formula I where Z=OH may by acylated, alkylated or converted into a compound where Z=F, Cl or Br, and, if appropriate, oxidized on the sulfur of a thioether group to form the sulfoxide or sulfone and, if appropriate, converted into the salt with a physiologically acceptable acid, as specified in the process above.

The compounds of the formula I, their acid-addition salts and their physiologically hydrolyzable derivatives are valuable medicaments. In particular, they have an anti-microbial action and are suitable for the prevention and treatment of fungal infections in humans and in various species of mammal.

The new compounds have a very good action in vitro against dermatophytes, such as, for example, *Trichophyton mentagrophytes, Microsporum canis* and *Epidermophyton floccosum*; against mold fungi, such as, for example, *Aspergillus niger*, or against yeasts, such as, for example, *Candida albicans, C. tropicalis, Torulopsis glabrata* and *Trichosporon cutaneum*, or against protozoa, such as *Trichomonas vaginalis* or *T. fetus*, or against Gram-positive and Gram-negative bacteria.

After oral or parenteral administration, the compounds also have a very good systemic effect in vivo, for example in experimental kidney candidiasis of the mouse, for example against *Candida albicans*. There is likewise a very good effect against various pathogens of dermatomycosis (for example *Trichophyton mentagrophytes*) in guinea pigs after oral, parenteral or local administration.

The following may be mentioned as examples of areas of indication in human medicine:

Dermatomycoses and systemic mycoses caused by *Trichophyton mentagrophytes* and other Trichophyton species, Microsporon species, Epidermophyton floccosum, gemmiparous fungi, biphasic fungi and mold fungi.

The following may be mentioned as areas of indication in veterinary medicine:

All dermatomycoses and systemic mycoses, particularly those which are caused by the abovementioned pathogens.

The present invention includes pharmaceutical preparations which contain, besides nontoxic, inert pharmaceutically suitable excipients, one or more active compounds according to the invention or which comprise one or more active compounds according to the invention, and also processes for the preparation of these preparations.

Nontoxic, inert pharmaceutically suitable excipients are taken to mean solid, semisolid or liquid diluents, fillers and formulation auxiliaries of all types.

Suitable forms of administration are, for example, tablets, dragees, capsules, pills, aqueous solutions, suspensions and emulsions, optionally sterile injectable solutions, nonaqueous emulsions, suspensions and solutions, ointments, creams, pastes, lotions, sprays etc.

The therapeutically active compounds should preferably be present in the abovementioned pharmaceutical preparations in a concentration from about 0.1 to 99.5, preferably from about 0.5 to 95% by weight of the total mixture.

In addition to the active compounds according to the invention, the abovementioned pharmaceutical preparations may also contain further pharmaceutical active compounds.

The abovementioned pharmaceutical preparations are prepared in a conventional fashion by known methods, for example by mixing the active compound or compounds with the excipient or excipients.

The present invention also includes the use of the active compounds according to the invention and of pharmaceutical preparations which contain one or more active compounds according to the invention in human and veterinary medicine for the prevention, improvement and/or curing of the abovementioned disorders.

The active compounds or the pharmaceutical preparations may be administered locally, orally, parenterally, intraperitoneally and/or rectally.

In order to achieve the desired results, it has generally proven advantageous, both in human and in veterinary medicine, to administer the active compound or active compounds in total amounts of at least about 0.05, preferably 0.1, particularly 0.5, mg and at most 200, preferably 100, particularly 10, mg/kg of body weight per 24 hours, based on an adult weighing 75 kg, if appropriate in the form of several individual doses. The total amount is administered in 1 to 8, preferably in 1 to 3, individual doses.

However, it may be necessary to deviate from the dosages mentioned, and in particular to do so as a function of the type and body weight of the object to be treated, the nature and the severity of the disorder, the type of the preparation and administration of the medicament, and the period of time or interval within which the administration takes place. Thus, it may in some cases be sufficient to manage with less than the abovementioned amount of active compound, whereas in other cases the abovementioned amount of active compound must be exceeded. The optimum dosage and type of administration of the active compounds required in each case can easily be determined by any expert on the basis of his expert knowledge.

The new compounds of the general formula (I), preferably the triazole compounds in which W denotes nitrogen, are also active as biocides. They are distinguished, in particular, by their fungicidal action in the case of phytopathogenic fungi. Even fungal pathogens which have already penetrated into the vegetative tissue can be combated successfully. This is particularly important and advantageous in those fungal diseases which cannot be combated effectively after the infection has occurred using the fungicides which are otherwise conventional. The spectrum of action of the new compounds covers a large number of different phytopathogenic fungi, such as, for example, *Piricularia oryzae, Plasmopara viticola,* various species of rust, but above all *Venturia inaequalis, Cercospora beticola* and true mildew fungi in fruit, vegetable, cereal and ornamental plant growing.

The new compounds of the general formula (I) are furthermore suitable for use in industrial fields, for example as wood-protection agents, as preservation agents in paints, in cooling lubricants for metalworking, or as preservatives in drilling and cutting oils.

The new compounds may be used in the conventional preparations as wettable powders, emulsifiable concentrates, sprayable solutions, powders, dressing agents, dispersions, granules or microgranules.

Wettable powders are taken to mean preparations which can be dispersed uniformly in water and which, besides the active compound and in addition to, if appropriate, a diluent or inert substance, contain wetting agents, for example polyoxethylated alkylphenols, polyoxethylated fatty alcohols, alkylsulfonates or alkylphenylsulfonates, and dispersing agents, for example sodium ligninsulfonate, sodium 2,2'-dinaphthylmethane-6,6'-disulfonate, sodium dibutylnaphthalenesulfonate or sodium oleoylmethyltaurinate. They are prepared in a conventional fashion, for example by grinding and mixing the components.

Emulsifiable concentrates may be prepared, for example, by dissolving the active compound in an inert organic solvent, for example butanol, cyclohexanone, dimethylformamide, xylene or higher-boiling aromatics or hydrocarbons, with addition of one or more emulsifiers. In the case of liquid active compounds, all or part of the solvent may be omitted. The following may be used, for example, as emulsifiers: calcium salts of alkylarylsulfonic acid, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitan fatty acid esters, polyoxethylene sorbitan fatty acid esters or polyoxethylene sorbitol esters.

Powders are obtained by grinding the active compound with finely divided, solid substances, for example talc, natural clays, such as kaolin, bentonite, pyrophillite or diatomaceous earth.

Granules can be prepared either by spraying the active compound onto adsorptive, granulated inert material or by applying the active compound concentrates onto the surface of excipients such as sand, kaolinite or granulated inert material by means of binders, for example polyvinyl alcohol, sodium polyacrylate or mineral oils. Suitable active compounds may also be granulated in the fashion which is conventional for the preparation of fertilizer granules—if desired as a mixture with fertilizers.

The active compound concentration in wettable powders is, for example, about 10–90% by weight, the rest to 100% by weight comprising conventional formulation components. The active compound concentration may be about 10–80% by weight of active compound in the case of emulsifiable concentrates, and about 1–20% by weight in the case of sprayable solutions. In the case of granules, the active compound content depends partly on whether the active compound is liquid or solid and which granulation auxiliaries, fillers etc. are used.

In addition, the active compound formulations mentioned contain, if appropriate, the adhesives, wetting agents, dispersing agents, emulsifiers, penetrants, solvents, fillers or excipients which are conventional in each case.

For use, the concentrates, present in commercially available form, are, if appropriate, diluted in a conventional fashion, for example using water in the case of wettable powders, emulsifiable concentrates, dispersions and, in some cases, microgranules. Powdered and granulated preparations and sprayable solutions are usually not further diluted with inert substances before use.

Mixtures or mixed formulations with other active compounds such as, for example, insecticides, acaricides, herbicides, fertilizers, growth regulators or further fungicides are possible if desired, it being possible to achieve synergistic increases in action under certain circumstances.

Some formulation examples may be given below:

A powder is obtained by mixing 10 parts by weight of active compound and 90 parts by weight of talc as inert substance and grinding in a hammer mill.

A wettable powder which is easily dispersible in water is obtained by mixing 25 parts by weight of active compound, 65 parts by weight of kaolin-containing quartz as inert substance, 10 parts by weight of potassium ligninsulfonate and 1 part by weight of sodium oleoylmethyltaurinate as wetting and dispersing agent and grinding in a pin mill.

A dispersion concentrate which is easily dispersible in water is prepared by mixing 20 parts by weight of active compound with 6 parts by weight of alkylphenol polyglycol ether (Triton X 207), 3 parts by weight of isotridecanol polyglycol ether (8 EO) and 71 parts by weight of paraffinic mineral oil (boiling range, for example, about 255° to above 377° C.) and grinding in an attrition ball mill to a fineness of below 5 microns.

An emulsifiable concentrate can be prepared from 15 parts by weight of active compound, 75 parts by weight of cyclohexanone as solvent and 10 parts by weight of oxethylated nonylphenol (10 EO) as emulsifier.

The following Examples serve to illustrate the invention in greater detail, without limiting it.

EXAMPLE 1

1-[1-(4-chlorophenyl)-1-hydroxy-2-(1,2,4-triazol-1-yl)ethyl]-1-octylthiocyclopropane

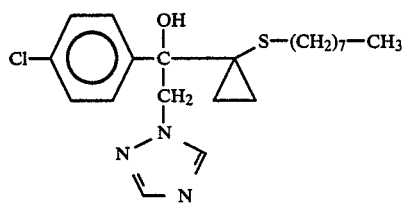

2.1 g=55 mmol of trimethylsulfoxonium iodide were added in portions at 20° C. with cooling and stirring to a suspension of 1.65 g=55 mmol of sodium hydride (80% strength suspension in oil) in 70 ml of dry dimethyl sulfoxide, and the mixture was stirred until cessation of the hydrogen evolution. A solution of 16.2 g=50 mmol of 1-(4-chlorobenzoyl)-1-octylthiocyclopropane in 20 ml of dry dimethyl sulfoxide was subsequently quickly added dropwise, and the mixture was stirred for one hour at room temperature and one hour at 40° C. 5.2 g=75 mmol of 1,2,4-triazole and then 2.3 g=25 mmol of the sodium salt of 1,2,4-triazole were subsequently added in portions and the mixture was stirred for 2 hours at 50° C. and 6 hours at 80° C. For work-up, the solution was poured into three times the amount of ice water and extracted with methylene chloride, and the organic phase was washed twice with 50 ml of 2N NaOH, dried using sodium sulfate and concentrated in a water-pump vacuum. The oil remaining was dissolved in 20 ml methanol, whereupon the substance crystallized. 12.2 g (60% of theory) of melting point 117°–118° C. (from methanol) were obtained.

Preparation of the starting materials 1-(4-chlorobenzoyl)-1-octylthiocyclopropane

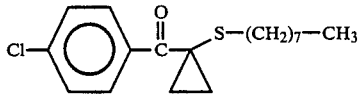

A solution of 17.8 g=60 mmol of 1-bromo-3-chloropropyl4-chlorophenyl ketone in 40 ml of acetone was added dropwise at 0° C. under a nitrogen atmosphere with stirring and cooling to a solution of 8.8 g=60 mmol of octyl mercaptan and 7 g=70 mmol of triethylamine in 60 ml of acetone, and the mixture was allowed to warm to room temperature and stirred for 15 hours. The resultant precipitate was filtered off under suction, washed with acetone and discarded. The organic phase was concentrated in a water-pump vacuum, the oily residue (compound of the formula VII) was taken up in 50 ml of methylene chloride, 20 ml of 50% sodium hydroxide solution and 0.4 g of tetrabutylammonium bromide were added, and the mixture was refluxed for 8 hours with vigorous stirring. 100 ml of water were added with stirring to the cold mixture, and work-up was effected as described above. The residue obtained (19 g) was distilled in an oil-pump vacuum. 16.1 g (82% of theory) of boiling point 165°–170° C. at 0.1 torr were obtained.

1-bromo-3-chloropropyl 4-chlorophenyl ketone

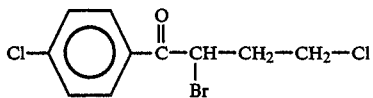

192 g=1.2 mol of bromine were added dropwise at 30° C. with stirring and cooling to a solution of 262 g=1.2 mol of 3-chloropropyl 4-chlorophenyl ketone in 480 ml of glacial acetic acid, the mixture was stirred for 4 hours at room temperature, and the precipitate was filtered off under suction, washed with cold diisopropyl ether and dried, and 335 g (94% of theory) of melting point: 73°–74° C. were obtained.

The other 1-bromo-3-chloropropyl ketones used as starting materials were prepared according to the example above.

EXAMPLE 2

1-[1-(4-chlorophenyl)-1-hydroxy-2-(imidazol-1-yl)-ethyl]-1-(4-chlorophenoxy)-cyclopropane

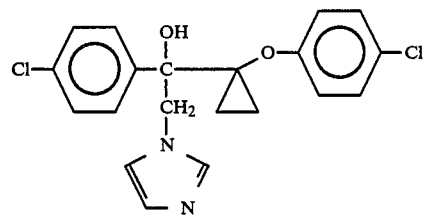

(a)
2-(4-chlorophenyl)-2-[1-(4-chlorophenoxy)-cyclopropan-1-yl]-oxirane (compound of the formula IV).

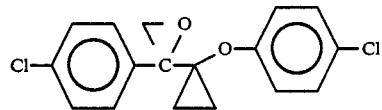

55 mmol of sodium hydride, 55 mmol of trimethylsulfoxonium iodide and 15.4 g=50 mmol of 1-(4-chlorobenzoyl)-1-(4-chlorophenoxy)-cyclopropane were initially reacted with one another in a dry dimethyl sulfoxide, and worked up as specified in Example 1. After trituration of the oily residue with ether, 11.2 g (70% of theory) of melting point: 97° C. crystallized out.

(b)
1-[1-(4-chlorophenyl)-1-hydroxy-2-(imidazol-1-yl)-ethyl]-1-(4-chlorophenoxy)-cyclopropane 11.2 g=35.5 mmol of the oxirane above were heated to 110° C. with stirring with 7.2 g=106.5 mmol of imidazol in the absence of a solvent. At this temperature, an exothermic reaction up to about 130° C. commenced. The heat source was removed until the internal temperature again reached 110° C., the mixture was subsequently stirred for 2 hours at 120° C., and the hot mixture was poured into three times the amount of ice water and worked up as specified in Example 1. After trituration of the resinous residue with ether, 11 g (80% of theory) of melting point: 172°–173° C. crystallized.

The preparation of the starting material 1-(4-chlorobenzoyl)-1-(4-chlorophenoxy)-cyclopropane A solution of 14.8 g=50 mmol of 1-bromo-3-chloropropyl4-chlorophenyl ketone in 30 ml of acetonitrile was added dropwise at room temperature with stirring to a suspension of 17.2 g=125 mmol of powdered potassium carbonate and 6.4 g=50 mmol of p-chlorophenol in 60 ml of acetonitrile. The mixture was stirred for 5 hours at room temperature, 0.4 g of tetrabutylammonium bromide was added, and the mixture was refluxed for 10 hours and worked up as specified in Example 1, and 12.6 g (82% of theory) of melting point: 69°-71° C. (from methanol) were obtained.

EXAMPLE 3

1-[1-(4-methylphenyl)-1-hydroxy-2-(4-chlorophenylthio)-ethyl]-1-(imidazol-1-yl)-cyclopropane

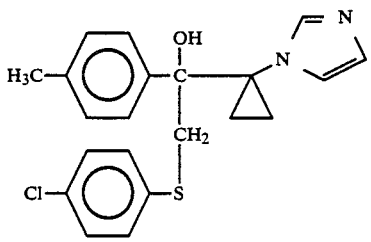

55 mmol of sodium hydride, 55 mmol trimethylsulfoxonium iodide and 12.0 g=50 mmol of 1-(4-methylbenzoyl)-1 -(imidazol-1-yl)-cyclopropane were initially reacted with one another, as specified in Example 1, in dry dimethyl sulfoxide, and a solution of the corresponding oxirane of the formula IV was obtained. A solution of 7.2 g=50 mmol of p-chlorothiophenol in 15 ml of dry dimethylsulfoxide was added dropwise to this under a nitrogen atmosphere at 20° C., and the mixture was stirred for a further 4 hours at 50° C. and worked up as specified in Example 1. After trituration of the resinous residue with methanol, 12.1 g (63% of theory) of melting point: 158°-160° C. crystallized.

Preparation of the starting material 1-(4-methylbenzoyl)-1-(imidazol-1-yl)-cyclopropane 82.6 g=0.3 mol of 1-bromo-3-chloropropyl 4-methylphenyl ketone were added in portions at 0°-5° C. with stirring and cooling to a solution of 102 g=1.5 mol of imidazole in 150 ml of dimethylformamide, and the mixture was stirred for 15 hours at room temperature. For work-up, the mixture was poured into 1.5 liters of ice water and extracted twice with 150 ml of methylene chloride in each case, and the organic phase was washed twice with 100 ml of 2N NaOH in each case, dried over sodium sulfate and filtered. The solution thus prepared of the corresponding compound of the formula VII was added dropwise at 20° C. with vigorous stirring and cooling to a mixture of 70 ml of 50% strength sodium hydroxide solution and 1.6 g of tetrabutylammonium bromide, and the mixture was stirred for 8 hours at 20° C. and worked up as specified in Example 1. The oily residue (66.5 g, 98% of theory) crystallized. A sample of this had the melting point: 88°-90° C. from methyl tert.butyl ether.

EXAMPLE 4

The compounds the formula I where Z=OH which are listed in Table 1 can also be prepared analogously to Example 1, 2 or 3, but using appropriate compounds of the formula II and Y-M. In column 2 (version), it is specified whether the procedure according to Example 1, 2 or 3 was used.

TABLE 1
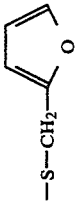
1. NaHS(CH₃)₃J
2. $Y_b$—M/DMSO
(where z = OH)
a and b indicate the positions of the Y radical;
Im denotes 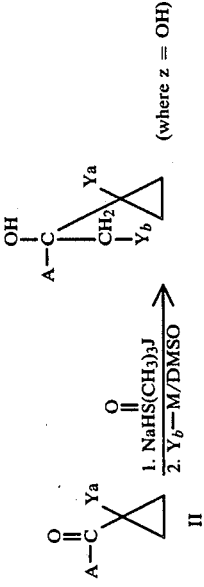, Triaz denotes 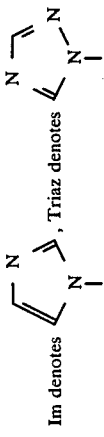
| Example No. | Version | A | $Y_a$ | $Y_b$ | m.p. (°C.) |
|---|---|---|---|---|---|
| 1.1 | 1 | —C₆H₄—4-Cl | —S—(CH₂)₇—CH₃ | Im | 99-101 |
| 1.2 | 1 | " | —S—(CH₂)₃—CH₃ | Im | 116-118 |
| 1.3 | 1 | " | —S—(CH₂)₃—CH₃ | Triaz | 143-144 |
| 1.4 | 1 | —C₆H₃—2,4-Cl₂ | —S—(CH₂)₃—CH₃ | Im | 167-172 |
| 1.5 | 1 | —C₆H₄—4-Cl | —S—CH₂—furyl | Triaz |  |
| 1.6 | 1 | " | —S—CH₂—phenyl | Im | 161-162 |
| 1.7 | 1 | " | " | Triaz |  |
| 1.8 | 1 | —C₆H₄—4-F | " | Triaz |  |
| 1.9 | 1 | —C₆H₃—2,4-F₂ | " | Triaz | 185-186 |
| 1.10 | 1 | —C₆H₄—4-Cl | —S—CH₂—(4-Cl-C₆H₄) | Im |  |
| 1.11 | 1 | —C₆H₄—4-Cl | " | Triaz | 184-185 |

TABLE 1-continued

| No. | | R | Ar-S-CH₂ group | Het | mp |
|---|---|---|---|---|---|
| 1.12 | 1 | —C₆H₄—4-Cl | —S—CH₂—C₆H₃(2-Cl)(4-Cl) | Im | |
| 1.13 | 1 | —C₆H₄—4-Cl | —S—CH₂—C₆H₄—4-Cl | Triaz | 155 |
| 1.14 | 1 | —C₆H₃—2,4-Cl₂ | " | Im | Oil |
| 1.15 | 1 | —C₆H₃—2,4-Cl₂ | —S—CH₂—C₆H₄—4-Cl | Triaz | |
| 1.16 | 1 | —C₆H₃—2,4-F₂ | —S—CH₂—C₆H₄—4-F | Triaz | 124–126 |
| 1.17 | 1 | " | | Im | 174–175 |
| 1.18 | 1 | —C₆H₄—Cl | —S—CH₂—C₆H₄—4-F | Triaz | 168–70 |
| 1.19 | 1 | " | —S—CH₂—C₆H₄—4-OCH₃ | Triaz | |
| 1.20 | 1 | —C₆H₄—4-F | —S—CH₂—C₆H₄—4-Cl | Im | 170–171 |
| 1.21 | 1 | " | | Triaz | 168–169 |
| 1.22 | 1 | —C₆H₄—4-OCH₃ | " | Im | 157–159 |
| 1.23 | 1 | —C₆H₄—4-CH₃ | " | Triaz | 171–173 |
| 1.25 | 1 | —C₆H₅ | " | Triaz | |
| 1.26 | 1 | | " | Triaz | |
| 1.27 | 1 | —C₆H₄—4-Cl | —S—CH₂—CH₂—C₆H₄—4-Cl | Triaz | |

TABLE 1-continued
| | | | | | |
|---|---|---|---|---|---|
| 1.28 | 1 | —C$_6$H$_4$—4-Cl | 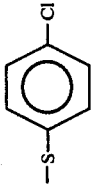 | Im | 164–165 |
| 1.29 | 1 | " | " | Triaz | 128–129 |
| 1.30 | 1 | —C$_6$H$_4$—4-Cl | 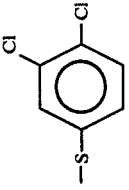 | Im | 152–154 |
| 1.31 | 1 | " |  | Im | 189–190 |
| 1.32 | 1 | " | " | Triaz | 185–188 |
| 1.33 | 1 | " |  | Triaz | |
| 1.34 | 1 | —C$_6$H$_4$—4-Cl | 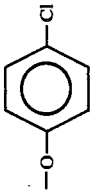 | Triaz | 160–165 |
| 1.35 | 2 | " | 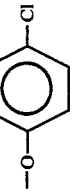 | Im | 170–173 |
| 1.36 | 2 | " | 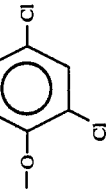 | Im | 209–210 |
| 1.37 | i | " |  | Triaz | |

TABLE 1-continued

| | | | | | |
|---|---|---|---|---|---|
| 1.38 | 2 | " | 2,4-Cl$_2$-C$_6$H$_3$-O-C$_6$H$_4$-O— | Im | 180–182 |
| 1.39 | 2 | " | 4-C$_6$H$_5$-C$_6$H$_4$-O— | Im | 168–170 |
| 1.40 | 1 | " | 2,4-Cl$_2$-C$_6$H$_3$-O-CH$_2$— | Triaz | 135–137 |
| 1.41 | 1 | " | 4-Cl-C$_6$H$_4$-O-CH$_2$— | Triaz | |
| 1.42 | 1 | " | C$_6$H$_5$-S-CH$_2$— | Triaz | |
| 1.43 | 1 | 5-Cl-thien-2-yl | 4-Cl-C$_6$H$_4$-S-CH$_2$— | Triaz | |
| 1.44 | 1 | " | 4-CF$_3$-C$_6$H$_4$-O— | Triaz | 195–196 |
| 1.45 | 2 | —C$_6$H$_4$-4-Cl | C$_6$H$_5$-SO$_2$— | Im | |
| 1.46 | 1 | —C$_6$H$_4$-4-Cl | | Im | |

TABLE 1-continued
| | | | | | |
|---|---|---|---|---|---|
| 1.47 | 1 |  | —S—CH₂——Cl | Triaz | |
| 1.48 | 1 |  | " | Triaz | |
| 1.49 | 1 |  | " | Triaz | |
| 1.50 | 1 |  | " | Triaz | |
| 1.51 | 1 |  | " | Triaz | |
| 1.52 | 3 | C₆H₄—4-Cl |  | Im | 196–198 |
| 1.52 | 3 | " |  | Triaz | |
| 1.53 | 3 | " | | Triaz | 135–137 |
| 1.54 | 3 | " | | Triaz | |

TABLE 1-continued

| No. | n | R | N-group | triazole | mp |
|---|---|---|---|---|---|
| 1.55 | 3 | " | | | |
| 1.56 | 1 | C6H4—4-F | Im | Im | 221–223 |
| 1.57 | 1 | " | Triaz | Im | 191–192 |
| 1.58 | 1 | C6H3—2,4-F2 | Im | Im | 204–206 |
| 1.59 | 1 | C6H3—2,4-F2 | Im | Triaz | 193–194 |
| 1.60 | 1 | | Triaz | Im | 205–207 |
| 1.61 | 1 | (thienyl) | Triaz | Triaz | 140–141 |
| 1.62 | 1 | (5-Cl-thienyl) | Triaz | Triaz | 181–183 |
| 1.63 | 1 | (indanyl) | Triaz | Triaz | |
| 1.65 | 1 | (tetrahydronaphthyl) | Triaz | Triaz | |
| 1.66 | 1 | (naphthyl) | Triaz | Triaz | |
| 1.67 | 1 | (biphenyl) | Triaz | Triaz | |
| 1.68 | 1 | (4-F-phenoxyphenyl) | Triaz | Triaz | |
| 1.69 | 3 | C6H4—4-Cl | Im | —S—(CH2)2—CH3 | |

TABLE 1-continued

| | | | | | m.p. °C |
|---|---|---|---|---|---|
| 1.70 | 3 | " | " | —S—(CH$_2$)$_3$—CH$_3$ | 87–88 |
| 1.71 | 3 | " | Triaz | " | 128–129 |
| 1.72 | 3 | " | Im | —S—C(CH$_3$)$_3$ | 140–146 decomp. |
| 1.73 | 3 | " | Im.HNO$_3$ | —S—CH$_2$—[furan] | |
| 1.74 | 3 | " | Im | —S—CH$_2$—[phenyl] | 145–146 |
| 1.75 | 3 | " | Im | —S—CH$_2$—[C$_6$H$_4$-Cl] | 138–139 |
| 1.76 | 3 | " | Triaz | " | 165–166 |
| 1.77 | 3 | " | Im | —S—CH$_2$—[C$_6$H$_3$-Cl$_2$] | 147–148 |
| 1.78 | 3 | C$_6$H$_4$—4-Cl | Im | —S—[phenyl] | |
| 1.79 | 3 | " | Im | —S—[C$_6$H$_4$-F] | 150–152 |
| 1.80 | 3 | " | Im | —S—[C$_6$H$_4$-Cl] | |
| 1.81 | 3 | " | Triaz | " | 131–133 |

TABLE 1-continued

| No. | | | | Structure | m.p. |
|---|---|---|---|---|---|
| 1.82 | 3 | " | Im | -S-C6H4-Br (4-Br phenylthio) | |
| 1.83 | 3 | " | Im | -S-C6H4-CH3 (4-methylphenylthio) | |
| 1.84 | 3 | " | Im | -S-C6H3-2,6-Cl2 (2,6-dichlorophenylthio) | |
| 1.85 | 3 | " | Im | -S-naphthyl | 137 |
| 1.86 | 3 | " | Triaz | " | 186-188 |
| 1.87 | 3 | $C_6H_3$—2,4-$Cl_2$ | Im | -S-C6H4-4-Cl | 158-160 |
| 1.88 | 3 | $C_6H_4$—4-$CH_3$ | Im | " | 166-168 |
| 1.89 | 3 | $C_6H_4$—4-F | Im | " | 161-162 |
| 1.90 | 3 | $C_6H_4$—4-$OCH_3$ | Im | " | 156-158 |
| 1.91 | 3 | $C_6H_5$ | Im | " | |
| 1.92 | 3 | $C_6H_4$—4-Cl | Im | -S-C(=N-)- (benzothiazolyl thio) | Oil |
| 1.93 | 3 | " | Im | -S-pyridyl | 112-114 |

TABLE 1-continued

| | | | | m.p. |
|---|---|---|---|---|
| 1.94 | 3 | C$_6$H$_4$—4-Cl | Im | [2-pyridyl-S-] 159-160 |
| 1.95 | 3 | " | Im | [4-Cl-C$_6$H$_4$-O-] 195-196 |
| 1.96 | 3 | " | Triaz | " |
| 1.97 | 3 | " | Im | [2,4-Cl$_2$-C$_6$H$_3$-O-] |
| 1.98 | 3 | " | Im | [2-Cl-4-(4-MeO-C$_6$H$_4$-O)-C$_6$H$_3$-] 98-99 |
| 1.99 | 3 | " | Im | [4-(4-MeO-C$_6$H$_4$)-C$_6$H$_4$-] 107-209 |
| 1.100 | 3 | " | Im | O—C$_2$H$_5$ 139-140 |
| 1.101 | 3 | " | Im | O—(CH$_2$)$_3$—CH$_3$ |
| 1.102 | 3 | " | Im | [4-phenyl-piperazinyl] Oil |
| 1.103 | 1 | C$_6$H$_3$—2,4-F,Cl | Triaz | [4-Cl-C$_6$H$_4$-CH$_2$-S-] 130-131 |
| 1.104 | 1 | C$_6$H$_3$—2,4-Cl,F | Triaz | " |

TABLE 1-continued

| No. | | R | Substituent | Ring | m.p. (°C) |
|---|---|---|---|---|---|
| 1.105 | 1 | C$_6$H$_4$—4-F | —S—CH$_2$—C$_6$H$_3$(2,4-Cl$_2$) | Triaz | |
| 1.106 | 1 | " | —S—CH$_2$—C$_6$H$_4$-3-Cl | Triaz | |
| 1.107 | 1 | " | —S—CH$_2$—C$_6$H$_4$-4-F | Triaz | |
| 1.108 | 1 | " | —S—CH$_2$—C$_6$H$_4$-4-OCH$_3$ | Triaz | 180–183 |
| 1.09 | 1 | —C$_6$H$_4$—4-F | —S—CH$_2$-(2-naphthyl) | Triaz | |
| 1.110 | 1 | " | —S—CH$_2$—C$_6$H$_4$-2-Cl | Triaz | |
| 1.111 | 1 | " | —S—CH$_2$—C$_6$H$_4$-3-F | Triaz | |

TABLE 1-continued

| | | | | | |
|---|---|---|---|---|---|
| 1.112 | 1 | — | —S—CH$_2$—C$_6$H$_4$(2-F) | Triaz | |
| 1.113 | 1 | " | —O—CH$_2$—C$_6$H$_4$(4-Cl) | Triaz | |
| 1.114 | 1 | " | —O—CH$_2$—C$_6$H$_4$(4-F) | Triaz | |
| 1.115 | 1 | " | —S—CH$_2$—C$_6$H$_4$(4-F) | Triaz | |
| 1.115 | 1 | —C$_6$H$_3$—2,4-F$_2$ | —O—CH$_2$—C$_6$H$_4$(4-F) | Triaz | 102-4 |
| 1.116 | 1 | " | —S—CH$_2$—C$_6$H$_3$(2,4-Cl$_2$) | Triaz | |
| 1.117 | 1 | —C$_6$H$_4$—4-Cl | —S—CH$_2$—C$_6$H$_4$(3-Cl) | Triaz | |
| 1.118 | 1 | " | —S—CH$_2$—C$_6$H$_4$(2-Cl) | Triaz | |

TABLE 1-continued
| | | | | | |
|---|---|---|---|---|---|
| 1.119 | 1 |  |  | Triaz | |
| 1.120 | 1 | " | Triaz | Triaz | 208–10 |
| 1.121 | 1 | " |  | Triaz | 75–77 |
| 1.122 | 1 | " | " | Im | 160–162 |
| 1.123 | 1 | —C₆H₄—4-Cl |  | Triaz | |
| 1.124 | 1 | " |  | Triaz | 163–165 |
| 1.125 | 1 | " |  | Triaz | 136 |
| 1.126 | 1 | " |  | Triaz | 127–129 |

TABLE 1-continued
| | | | | m.p. °C |
|---|---|---|---|---|
| 1.127 | 1 | " |  | 188-191 |
| 1.128 | 1 | " | 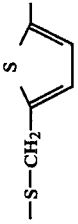 | 143-147 |
| 1.129 | 1 | " | 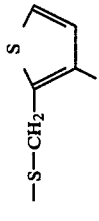 | 147-149 |
| 1.130 | 1 | " | 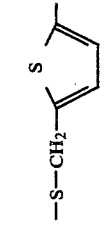 | 135-136 |
| 1.131 | 1 | " | 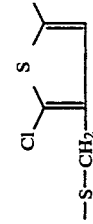 | 156-157 |
| 1.132 | 1 | " | 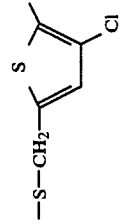 | 135-137 |
| 1.133 | 1 | " | 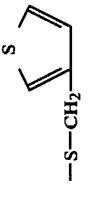 | 171-172 |
| 1.134 | 1 | —C$_6$H$_4$—4-Cl | 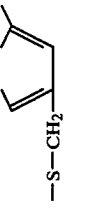 | Triaz 140-141 |
| 1.135 | 1 | " | 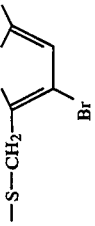 | 151-152 |

TABLE 1-continued
| | | | | |
|---|---|---|---|---|
| 1.136 | 1 | " | 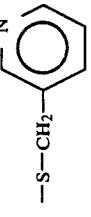 | 129–130 |
| 1.137 | 1 | " | 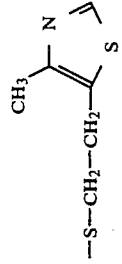 | 118–119 |
| 1.138 | 1 | " | 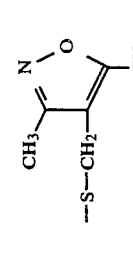 | 168–169 |
| 1.139 | 1 | " | 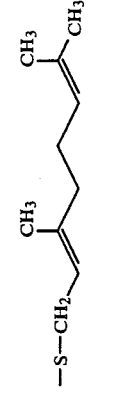 | 93–94 |
| 1.140 | 1 | " | 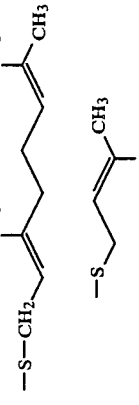 | imidazole | Oil |
| 1.141 | 1 | " |  | triazole | 144–145 |
| 1.142 | 1 | " | 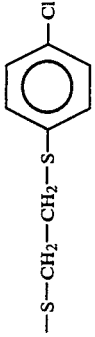 | " | 124–127 |
| 1.143 | 1 | " |  | " | 96–97 |
| 1.144 | 1 | —C$_6$H$_4$—4-F | 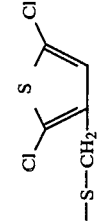 | triazole | 112–113 |

TABLE 1-continued

| No. | | | | | mp |
|---|---|---|---|---|---|
| 1.145 | 1 | " | —S—CH$_2$-(5-chlorothiophen-2-yl) | " | 138–139 |
| 1.146 | 1 | " | —S—CH$_2$-(5-chloro-3-bromothiophen-2-yl) | " | 123–125 |
| 1.147 | 1 | " | —S—CH$_2$-(5-chlorothiophen-3-yl) | " | 114–5 |
| 1.148 | 1 | " | —S—CH$_2$—CH$_2$—S—CH$_2$—C$_6$H$_5$ | " | 102–103 |
| 1.149 | 1 | " | —S—CH$_2$-(pyridin-4-yl) | " | 132–133 |
| 1.150 | 1 | " | —S—CH$_2$-(pyridin-2-yl) | Triaz | |
| 1.151 | 1 | —C$_6$H$_4$—4-Cl | —S—CH$_2$-(pyridin-3-yl) | " | 166–167 |
| 1.152 | 1 | " | —S—CH$_2$-(2,4-difluorophenyl) | Im | 150–152 |

TABLE 1-continued
| | | | | |
|---|---|---|---|---|
| 1.153 | 1 | " | 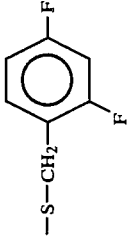 | Triaz | 137–139 |
| 1.154 | 1 | " | 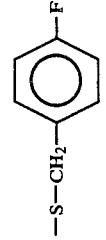 | Im | 170–171 |
| 1.155 | 1 | —C$_6$H$_4$—4-F | 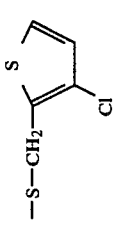 | Triaz | 151–152 |
| 1.156 | 1 | —C$_6$H$_4$—4-F | 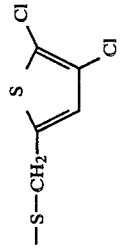 | Triaz | |
| 1.157 | 1 | —C$_6$H$_4$—4-OCH$_3$ | 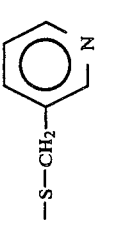 | Triaz | |
| 1.158 | 1 | —C$_6$H$_4$—4-F | 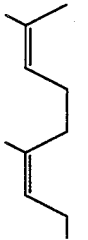 | " | 92–93 |
| 1.159 | 1 | —C$_6$H$_4$—4-Cl | 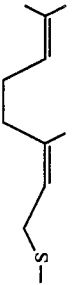 | " | 109–110 |
| 1.160 | 1 | " |  | " | 103–104 |

TABLE 1-continued

| No. | | R | Structure | | m.p. |
|---|---|---|---|---|---|
| 1.161 | 1 | —C₆H₄—4-F | —S—CH₂—CH₂—S—CH₂—C₆H₄—4-Cl | " | 98–100 |
| 1.162 | 1 | —C₆H₄—4-Cl | 2-Cl-thiophen-3-yl-CH₂—S— | " | |
| 1.163 | 1 | —C₆H₄—4-F | 2-Cl-thiophen-3-yl-CH₂—S— | " | |
| 1.164 | 1 | —C₆H₄—4-Cl | 5-Br-furan-2-yl-CH₂—S— | " | 131–132 |
| 1.165 | 1 | " | 6-Cl-pyridin-3-yl-CH₂—S— | " | |
| 1.166 | 1 | " | 2-Cl-pyridin-3-yl-CH₂—S— | " | |
| 1.167 | 1 | —C₆H₄—4-F | 6-Cl-pyridin-3-yl-CH₂—S— | Triaz | |
| 1.168 | 1 | C₆H₄—4-OCH₃ | 2,5-diCl-thiophen-3-yl-CH₂—S— | " | |
| 1.169 | 1 | " | 5-Cl-thiophen-2-yl-CH₂—S— | " | |

TABLE 1-continued
| | | | | |
|---|---|---|---|---|
| 1.170 | 1 | " | 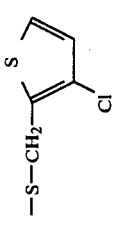 | 157–159 |
| 1.171 | 1 | C6H4—4-t-butyl | 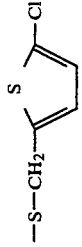 | 143–144 |
| 1.172 | 1 | " | 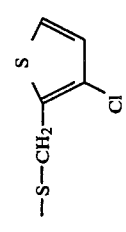 | |
| 1.173 | 1 | " | 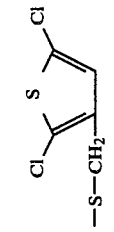 | |
| 1.174 | 1 | —C6H4—4-Cl | 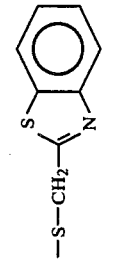 | |
| 1.175 | 1 | —C6H4—4-Cl | 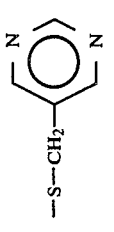 | |
| 1.176 | 1 | —C6H4—4-F | 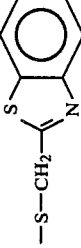 | |
| 1.177 | 1 | 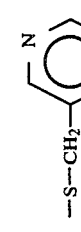 | 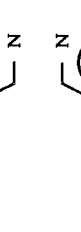 | 116–117 |
| 1.178 | 1 | 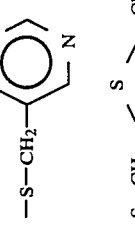 | 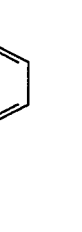 | Triaz |

TABLE 1-continued
| | | | | |
|---|---|---|---|---|
| 1.179 |  | 1 |  | " |
| 1.180 |  | 1 |  | " |
| 1.181 |  | 1 |  | " |
| 1.182 |  | 1 | " | 146-147 |
| 1.183 |  | 1 |  | " |
| 1.184 |  | 1 |  | " |
| 1.185 |  | 1 |  | " 130-131 |
| 1.186 | —C₆H₄—4-Cl | 1 |  | " 148-150 |

TABLE 1-continued

| | | | | |
|---|---|---|---|---|
| 1.187 | 1 | —C$_6$H$_3$—2,4-F$_2$ | —S—CH$_2$-(5-chlorothiophen-2-yl) | " |
| 1.188 | 1 | —C$_6$H$_3$—2,4-F$_2$ | —S—CH$_2$-(2,5-dichlorothiophen-3-yl) | " |
| 1.189 | 1 | " | —S—CH$_2$-(3-chlorothiophen-2-yl) | " |
| 1.190 | 1 | —C$_6$H$_4$—4-Cl | —S—CH$_2$-(pyridin-2-yl) | Triaz |
| 1.191 | 1 | —C$_6$H$_4$—4-CH$_3$ | —S—CH$_2$-(5-chlorothiophen-2-yl) | " |
| 1.192 | 1 | —C$_6$H$_4$—4-CH$_3$ | —S—CH$_2$-(2,5-dichlorothiophen-3-yl) | " |
| 1.193 | 1 | (5-chlorothiophen-2-yl) | —S—CH$_2$-(5-chlorothiophen-2-yl) | " |
| 1.194 | 1 | (5-chlorothiophen-2-yl) | —S—CH$_2$-(2,5-dichlorothiophen-3-yl) | " |
| 1.195 | 1 | (5-chlorothiophen-2-yl) | —S—CH$_2$-(3-chlorothiophen-2-yl) | " |

TABLE 1-continued

| | | | | m.p. °C |
|---|---|---|---|---|
| 1.196 | 1 | —C6H4—4-Cl | —S—CH2-(5-F-thienyl) | " |
| 1.197 | 1 | tetrahydronaphthyl | —S—CH2-(2-Cl-thienyl) | " |
| 1.198 | 1 | —C6H4—4-Cl | —S—CH2-(quinolinyl) | 143–145 |
| 1.199 | 1 | (5-Cl-thienyl) | —S—CH2-(3-Cl-thienyl) | " |
| 1.200 | 1 | —C6H4—4-Cl | —S-(thienyl) | " |
| 1.201 | 1 | —C6H4—4-Cl | —S—CH2-(2-Br-3-Cl-thienyl) | Triaz |
| 1.202 | 1 | —C6H4—4-F | —S-geranyl | " |
| 1.203 | 1 | tetrahydronaphthyl | —S—CH2-(thienyl) | 146–147 |
| 1.204 | 1 | tetrahydronaphthyl | —S—CH2-(pyridyl) | 130–131 |

TABLE 1-continued

| | | | | m.p. |
|---|---|---|---|---|
| 1.205 | 1 | —C$_6$H$_3$—2,4-F$_2$ | —S—CH$_2$-(thiophene) | " |
| 1.206 | 1 | (5-chlorothiophene) | —S—CH$_2$-(thiophene) | " |
| 1.207 | 1 | —C$_6$H$_4$—4-CH$_3$ | —S—CH$_2$-(3,4-dichlorothiophene) | " |
| 1.208 | 1 | (4'-fluorobiphenyl) | —S—CH$_2$-(3-chlorothiophene) | " |
| 1.209 | 1 | (tetrahydronaphthyl) | —S—CH$_2$—CH=C(CH$_3$)—CH$_2$CH$_2$CH=C(CH$_3$)$_2$ | " |
| 1.210 | 1 | (tetrahydronaphthyl) | —S—CH$_2$-(thiophene) | 144–145 |
| 1.211 | 1 | —C$_6$H$_4$—4-CH$_3$ | —S—CH$_2$-(thiophene) | 156–157 |
| 1.212 | 1 | —C$_6$H$_4$—4-CH$_3$ | —S—CH$_2$-(3-chlorothiophene) | 153–155 |
| 1.213 | 1 | —C$_6$H$_4$—4-OCH$_3$ | —S—CH$_2$-(pyridine) | 128–129 |

EXAMPLE 5

1-[1-(4-chlorophenyl)-1-methoxy-2-(imidazol-1-yl)-ethyl]-1-(4-chlorophenoxy)-cyclopropane

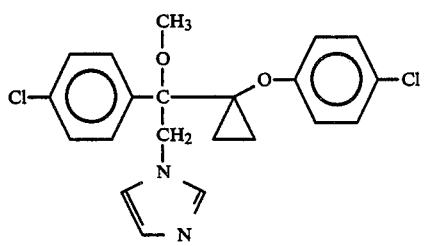

7.8 g=20 mmol of 1-[1-(4-chlorophenyl)-1-hydroxy-2-(imidazol-1-yl)-ethyl]-1-(4-chlorophenoxy)-cyclopropane (compound from Example 2) were added in portions at 20° C. to a suspension of 0.66 g=22 mmol of sodium hydride (80% strength suspension in oil) in 20 ml of dry dimethylformamide, and the mixture was stirred until cessation of hydrogen evolution. A solution of 3.1 g=22 mmol of methyl iodide in 5 ml of dry dimethylformamide was subsequently added dropwise at 0° C., and the mixture was allowed to warm to room temperature, stirred for a further 15 hours and worked up as specified in Example 1. The resinous residue (9.3 g) was purified over a silica gel column using methylene chloride: ethanol=20:1 as eluent. The residue produced from the uniform fractions crystallized on dissolution in ether. 4.4 g (55% of theory) of melting point: 117°–119° C. were obtained.

EXAMPLE 6

The compounds of the formula I listed in Table 2 can also be prepared analogously to Example 5, but using appropriate compounds of the formula I where Z=OH and using an alkyl halide or benzyl halide.

Im, Triaz, a and b have the same meaning as specified for Table 1.

TABLE 2

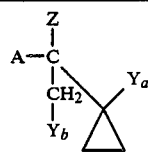

I

| Example No. | Prepared from | A | $Y_a$ | $Y_b$ | Z | m.p.: [°C.] |
|---|---|---|---|---|---|---|
| 2.1 | 1.29 | —C₆H₄—4-Cl | —S—⟨C₆H₃⟩—Cl | Triaz | —OCH₃ | 148–150 |
| 2.2 | 1.30 | " | —S—⟨C₆H₃⟩(Cl)—Cl | Im | " | Oil |
| 2.3 | 1.31 | " | —S—⟨naphthyl⟩ | Im | " | Oil |
| 2.4 | 1.35 | " | —O—⟨C₆H₃⟩(Cl)—Cl | Im | " | Oil |
| 2.5 | 1.38 | " | —O—⟨C₆H₄⟩—O—⟨C₆H₂⟩(Cl)(Cl)—Cl | Im | " | 180–182 |
| 2.6 | 1.11 | " | —S—CH₂—⟨C₆H₄⟩—Cl | Triaz | " | Oil |

TABLE 2-continued $$\underset{I}{A-\underset{\underset{Y_b}{|}}{\overset{\overset{Z}{|}}{\underset{\underset{CH_2}{|}}{C}}}-\triangleleft Y_a}$$

| Example No. | Prepared from | A | $Y_a$ | $Y_b$ | Z | m.p.: [°C.] |
|---|---|---|---|---|---|---|
| 2.7 | 1.80 | " | Im | —S—⟨C₆H₄⟩—Cl | " | 118–120 |
| 2.8 | 1.56 | " | Im | Im | —O—CH₂—⟨2,4-Cl₂-C₆H₃⟩ | 238–240 |
| 2.9 | 1.56 | " | " | " | —O—CH₂—⟨C₆H₄⟩—CF₃ | 182–187 |
| 2.10 | 1.62 | 5-Cl-thien-2-yl | Triaz | Triaz | OCH₃ | |
| 2.11 | 1.20 | —C₆H₄—4-F | —S—CH₂—⟨C₆H₄⟩—Cl | Triaz | OCH₃ | |
| 2.12 | 1.12 | —C₆H₄—4-Cl | —S—CH₂—⟨2-Cl-C₆H₃⟩—Cl | Triaz | OCH₃ | |

EXAMPLE 7

1-[1-(4-chlorophenyl)-1-chloro-2-(1,2,4-triazol-1-yl)ethyl]-1-(4-chlorobenzylthio)-cyclopropane

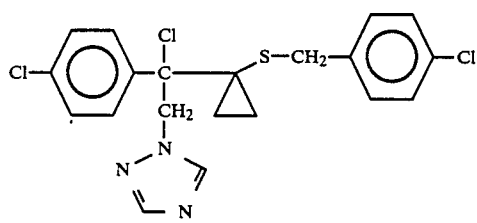

A solution of 4.2 g = 10 mmol of 1-[1-(4-chlorophenyl)-1-hydroxy-2-(1,2,4-triazol-1-yl)-ethyl]-1-(4-chlorobenzylthio)-cyclopropane (compound 1.11, Table 1) in 20 ml of dry methylene chloride was added dropwise at 0° C. with stirring and cooling to a solution of 4 g = 30 mmol of thionyl chloride in 30 ml of dry acetonitrile, and the mixture was stirred for 15 hours at 20° C. and for one hour under reflux. The mixture was subsequently concentrated in a water-pump vacuum, and the residue was dissolved in 100 ml of methylene chloride/30 ml of 2N NaOH, worked up as specified in Example 1, and chromatographed on a column as specified in Example 5. 1 g (22% of theory) of melting point: 88°–92° C. was obtained.

EXAMPLE 8

1-(4-chlorophenyl)-1-[1-(imidazol-1-yl)-cyclopropane-1-yl]1-hydroxyeth-2-yl benzyl sulfoxide

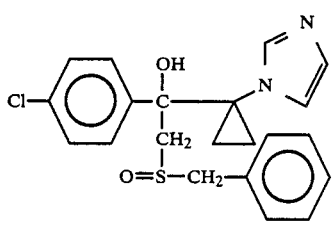

A solution of 1 g = 10 mmol of 35% strength hydrogen peroxide in 5 ml of glacial acetic acid was added dropwise at 0° C. with stirring and cooling to a solution of 3.8 g = 10 mmol of 1-[1-(4-chlorophenyl)-1-hydroxy-2- benzylthioethyl]-1-(imidazol-1-yl)-cyclopropane (compound 1.74, Table 1) in 20 mL of methylene chloride, and the mixture was allowed to warm to 20° C. within 3 hours, stirred for a further 15 hours and worked up as specified in Example 1. The resinous residue crystallized after standing for several days in ethyl acetate. 28 g (70% of theory) of melting point: 205°–207° C. (methanol) were obtained.

EXAMPLE 9

The compounds of the formula listed in Table 3 can be prepared analogously to Example 8. Im, Triaz, a and b have the same meaning as specified for Table 1.

EXAMPLE 10

1-[-1-(4-chlorophenyl-1-hydroxy-2-(1,2,4-triazol-1-yl)-ethyl]-1-(4-chlorobenzylsulfonyl)-cyclopropane

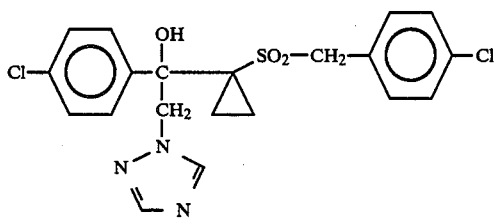

2.2 g=22 mmol of 35% strength hydrogen peroxide was added dropwise at 20° C. with stirring to a solution of 4.2 g=10 mmol of 1-[1-(4-chlorophenyl-1-hydroxy-2-(1,2,4-triazol-1-yL)-ethyl]-1-(4-chlorobenzylthio)-cyclopropane (compound 1.11, Table 1)in 30

TABLE 3

$$\begin{array}{c} OH \\ | \\ A-C \\ | \\ CH_2 \\ | \\ Y_b \end{array} \!\!\! \diagdown \!\! Y_a$$

I (where Z = OH)

| Example No. | Prepared from | A | $Y_a$ | $Y_b$ | m.p.: [°C.] |
|---|---|---|---|---|---|
| 3.1 | 1.11 | —C₆H₄—4-Cl | —S(O)—CH₂—C₆H₄—Cl | Triaz | (1) 208–209[a] (2) 197–198 |
| 3.2 | 1.21 | —C₆H₄—4-F | " | Triaz | |
| 3.3 | 1.16 | —C₆H₃—2,4-F₂ | " | Triaz | |
| 3.4 | 1.44 | thienyl-Cl | " | Triaz | |
| 3.5 | 1.15 | —C₆H₃—2,4-Cl₂ | " | Triaz | |
| 3.6 | 1.103 | —C₆H₃—2.4-F,Cl | " | Triaz | |
| 3.7 | 1.104 | —C₆H₃—2.4-Cl,F | " | Triaz | |
| 3.8 | 1.13 | —C₆H₄—4-Cl | —S(O)—CH₂—C₆H₃—2,4-Cl₂ | Triaz | (1) 210–214 (2) 201–204 |
| 3.9 | 1.18 | —C₆H₄—4-Cl | —S(=O)—CH₂—C₆H₄—F | Triaz | 175 |
| 3.10 | 1.127 | —C₆H₄—4-Cl | —S(O)—CH₂—thienyl | " | (1) 01 (2) 179–181 |
| 3.11 | 1.129 | " | —S(O)—CH₂—(Cl-thienyl) | " | |

[a]The pairs of diastereomers of the sulfoxides were separated by column chromatography as specified in Example 5. The (1) to (2) ratio is 1:3, where (1) represents the nonpolar component and is eluted first from the column.

ml of glacial acetic acid, and the mixture was subsequently stirred for 2 hours at 20° C. and 4 hours under reflux, and worked as specified in Example 1, 2.9 g (65% of theory) of melting point 189°–190° C. were obtained.

EXAMPLE 11

The compounds of the formula I listed in Table 4 can also be prepared analogously to Example 10.

Im, Triaz, a and b have the same meaning as specified for Table 1.

TABLE 4

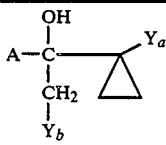

I (where Z = OH)

| Example No. | Prepared from | A | $Y_a$ | $Y_b$ | m.p.: [°C.] |
|---|---|---|---|---|---|
| 4.1 | 1.21 | —C$_6$H$_4$—4-F | —SO$_2$—CH$_2$—⟨C$_6$H$_4$⟩—Cl | Triaz | |
| 4.2 | 1.16 | —C$_6$H$_3$—2,4-F$_2$ | " | Triaz | |
| 4.3 | 1.44 | ⟨thiophene⟩—Cl | " | Triaz | |
| 4.4 | 1.15 | —C$_6$H$_3$—2,4-Cl$_2$ | " | Triaz | |
| 4.5 | 1.103 | —C$_6$H$_3$—2,4-F,Cl | " | Triaz | |

Examples of process version b of the second preparation process

EXAMPLE 12

Preparation of a compound of the formula V 1-(4-chlorophenyl)-1-[1-(4-chlorophenoxy)-cyclopropan-1-yl]-ethene

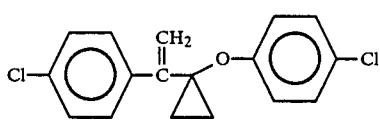

A suspension of 3 g=0.1 mol of sodium hydride (80% strength suspension in oil) and 50 ml of dry dimethyl sulfoxide was stirred at 60°–70° C. under a nitrogen atmosphere until the evolution of hydrogen was complete (about 1.5 hours). A solution of 40.4 g=0.1 mol of methyltriphenylphosphonium iodide in 100 ml of dry dimethyl sulfoxide was subsequently added dropwise at −10° C., the mixture was allowed to warm to 20° C., a solution of 30.7 g=0.1 mol of 1-(4-chlorobenzoyl)-1-(4-chlorophenoxy)-cyclopropane in 30 ml of dry dimethyl sulfoxide was added dropwise, and the mixture was stirred for one hour at 20° C., 4 hours at 60° C., and worked up as specified in Example 1. The residue was dissolved in the same volume of boiling ethyl acetate, the mixture was cooled using an ice bath, and the precipitate was filtered off under suction and washed with ether. The organic phase was concentrated in a water-pump vacuum, and the residue shaken three times with 100 ml of petroleum ether and decantered off. The petroleum ether phase was filtered through neutral alumina and concentrated in vacuo. 26 g of an oil, which were used in Example 14 without further purification, were obtained.

EXAMPLE 13

1-(4-chlorophenyl)-1-[1-(imidazol-1-yl)-cyclopropan-1-yl]-ethene 14.7 g (60% of theory) of melting point: 94°–95° C. were obtained according to Example 12, but using 1-(4-chlorobenzoyl)-1-(imidazol-1-yl)-cyclopropane.

EXAMPLE 14

Preparation of a compound of the formula IV 2-(4-chlorophenyl)-2-[1-(4-chlorophenoxy)-cyclopropan-1-yl]oxirane (cf. Example 2a).

A solution of 4.3 g=25 mmol of 80% strength m-chloroperbenzoic acid in 100 ml of chloroform was added dropwise at 20° C. with stirring to a solution of 6.1 g=20 mmol of 1-(4-chlorophenyl)-1-[1-(4-chlorophenoxy)-cyclopropan-1-yl]-ethene (compound from Example 12) in 20 ml of chloroform, and the mixture was stirred for 15 hours at 20° C. and 3 hours under reflux. For work-up, the mixture was shaken three times with 50 ml of 2N sodium hydroxide solution and once with 2N sodium bisulfite solution, washed with water and dried over sodium sulfate, and the solution was concentrated in a water-pump vacuum. The residue was dissolved in twice the volume of ether. After seeding using a crystal from Example 2a, 3.2 g of melting point 96°–97° C. crystallized.

EXAMPLE 15

2-(4-chlorophenyl)-2-[1-(imidazol-1-yl)-cyclopropan-1-yl]-oxirane

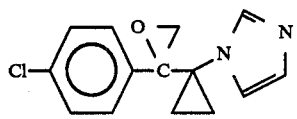

According to Example 14, but using 4.9 g=20 mmol of 1-(4-chlorobenzoyl)-1-(imidazol-1-yl)-cyclopropane, 4.5 g of an oil, which was used in Example 17 without further purification, were obtained.

EXAMPLE 16

Preparation of a compound of the formula I

1-[1-(4-chlorophenyl)-1-hydroxy-2-(imidazol-1-yl)-ethyl]-1-(4-chlorophenoxy)-cyclopropane 3.2 g=10 mmol of 2-(4-chlorophenyl)-2-[1-(4-chlorophenoxy)cyclopropan-1-yl]-oxirane (compound from Example 14) were reacted with 2.04 g=30 mmol of imidazol, as specified in Example 2a), in the absence of a solvent, and 2.9 g (75% of theory) of melting point: 172°–173° C. were obtained.

EXAMPLE 17

1-[1-(4-chlorophenyl)-1-hydroxy-2-(4-chlorophenylthio)-ethyl]-1-(imidazol-1-yl)-cyclopropane A solution of 2.4 g=17 mmol of p-chlorothiophenol in 10 ml of acetone was added dropwise at 20° C. under a nitrogen atmosphere and with stirring to a solution of 4.5 g=17.2 mmol of 2-(4-chlorophenyl)-2-[-(imidazol-1-yl)-cyclopropan- 1-yl]-oxirane (compound from Example 15) and 1.7 g=17 mmol of triethylamine in 20 ml of acetone, and the mixture was stirred for 2 hours at 20° C. and 5 hours under reflux and was worked up as specified in Example 1.

3.1 g (45% of theory) of melting point: 148°–150° C. (from methanol) were obtained.

Results of the treatment of laboratory animals infected experimentally with Candida albicans are given as an example of the high oral and parenteral in vivo action of the compounds according to the invention.

In order to determine the oral and parenteral activity, groups of 5 mice (strain HOE: NMRKF; SPF 71) weighing 18–20 g were infected with $2 \times 10^6$ germs/animal.

The animals were treated orally or subcutaneously in 8 identical individual doses of 30 mg/kg, 10 mg/kg or 2.5 mg/kg of bodyweight each (−24/−18/−2h/+2/24/30/48/54h).

Besides the group of 5 animals treated with the substances I according to the invention, a group, likewise of 5 animals, was treated for comparison with the reference substances ketoconazole or fluconazole. A control group of 10 animals remained untreated after infection.

As can be seen from Table 2, the animals survived for twice as long after infection in the case of the compounds 1.11 and 1.21 according to the invention, compared to the current standard preparation ketoconazole.

In the case of compounds 1.131 and 1.151, fluconazole is used as standard, the animals surviving for up to 50% longer.

TABLE 5

| Dose | Preparation Example No. | No. of animals | Survival times Days after infection | | | | | | | | | | x days | Survival time in % (standard prep. = 100%) |
|---|---|---|---|---|---|---|---|---|---|---|---|---|---|---|
| oral | 1.11 | 10 | 8 | 8 | 8 | 9 | 9 | 9 | 10 | 10 | 12 | 25 | 10,8 | 308,5 |
| 8 × 10 mg/kg | 1.21 | 10 | 8 | 8 | 9 | 9 | 9 | 9 | 9 | 10 | 11 | 12 | 8,9 | 254,2 |
| | ketoconazole | 10 | 2 | 3 | 3 | 3 | 3 | 4 | 4 | 4 | 4 | 5 | 3,5 | 100 |
| oral | 1.131 | 10 | 7 | 8 | 8 | 8 | 9 | 9 | 11 | 13 | 15 | 16 | 10,4 | 118,2 |
| 8 × 2,5 mg/kg | 1.151 | 10 | 9 | 9 | 10 | 13 | 15 | 15 | 17 | 18 | 18 | 13,4 | | 152,3 |
| | fluconazole | 10 | 7 | 7 | 7 | 8 | 8 | 8 | 10 | 11 | 11 | 11 | 8,8 | 100 |
| subcutaneous | 1.11 | 10 | 19 | 21 | 21 | 23 | 26 | 27 | 27 | 29 | 29 | 29 | 25,1 | 398,4 |
| 8 × 10 mg/kg | 1.21 | 10 | 13 | 13 | 20 | 20 | 20 | 21 | 26 | 28 | 31 | 33 | 22,5 | 357,1 |
| | ketoconazole | 10 | 5 | 5 | 5 | 6 | 6 | 6 | 6 | 7 | 8 | 9 | 6,3 | 100 |
| Controls, untreated infected animals | — | 10 | 1 | 1 | 2 | 2 | 2 | 2 | 2 | 2 | 3 | 3 | 2,0 | — |

We claim:

1. A compound of the formula I

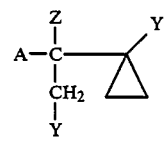

in which:
A is phenyl, biphenylyl, naphthyl, 1,2,3,4-tetrahydronaphthyl, indanyl, or fluorenyl, where the ring systems therein are unsubstituted or are substituted by 1–3 substituents which are identical or different and which are F, Cl, Br, I, $(C_1-C_8)$-alkyl which is straight-chain or branched, and which is unsubstituted, $CF_3$, $(C_3-C_8)$-cycloalkyl, $(C_1-C_8)$-alkoxy which is straight-chain or branched, and is unsubstitued, $(C_3-C_8)$cycloalkyl-$(C_1-C_4)$alkyl, $(C_1-C_8)$alkylthio, $(C_1-C_8)$-alkysulfinyl, $(C_1-C_8)$-alkylsulfonyl, $NO_2$ or $CN$;

Y connected to $CH_2$ is

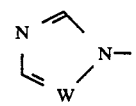

where W is CH or N, and
Y connected to the cyclopropyl group is (2a)

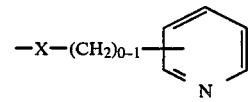

or (2b)

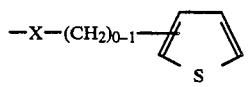

where X is —O—, —S—,

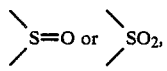

where the ring system of formula (2A) is unsubstituted or is substituted by 1, 2 or 3 substituents which are identical or different and in each case are F, Cl, Br, I, CF$_3$, (C$_1$–C$_4$)-alkyl or (C$_1$–C$_4$)-alkoxy, and where the ring system of formula (2b) is unsubstituted or is substituted by 1, 2 or 3 substituents which are identical or different and in each case are F, Cl, Br, (C$_1$–C$_4$)-alkyl, (Chd 1–C$_4$)-alkoxy or phenyl which is unsubstituted or is substituted by 1, 2, or 3 substituents which are identical or different and in each case are F, Cl, Br, (C$_1$–C$_4$)-alkyl or (C$_1$–C$_4$)-alkoxy; and Z is OH, (C$_1$–C$_4$)-alkylcarbonyloxy, F, Cl, Br, (C$_1$–C$_4$)-alkoxy or benzyloxy, unsubstituted or monosubstituted or disubstituted by F, Cl, Br or CF$_3$;

or a physiologically acceptable salt thereof.

2. A compound of the formula I as claimed in claim 1, wherein the following substituents have the following meaning:

A is phenyl, biphenylyl, 1,2,3,4-tetrahydronaphthyl, or indanyl, which are unsubstituted or are substituted in the ring by one or two substituents which are identical or different and in each case are F, Cl, Br, CF$_3$, (C$_1$–C$_4$)-alkyl or (C$_1$–C$_4$)-alkoxy;

Y connected to CH$_2$ is (1)

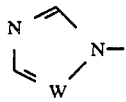

where W is CH or N, and

Y connected to the cyclopropyl group is (2a)

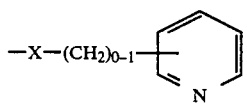

or (2b)

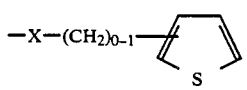

where X is O, S or

and where the ring systems of formulas (2a) and (2b) are unsubstituted or substituted by 1, 2 or 3 substituents which are identical or different and in each case are F, Cl, Br, CF$_3$, methyl or methoxy groups, Z is OH, OCH$_3$, F or Cl, or a physiologically acceptable salt thereof.

3. A compound of the formula as claimed in claim 1, wherein the following substituents have the following meaning:

A is phenyl which is unsubstituted or is substituted by 1 or 2 F or Cl atoms, methyl or methoxy Y connected to the CH$_2$ is (1)

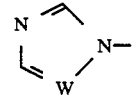

where W is CH or N, and

Y connected to the cyclopropyl group is (2a)

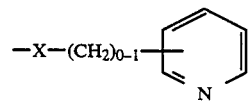

(2b)

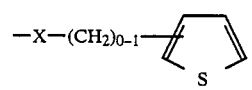

where X is O, S or

and the ring systems of formulas (2a) and (2b) are unsubstituted, or monosubstituted or disubstituted by F, Cl, methyl or methoxy; and Z is OH, or a physiologically acceptable salt thereof.

4. An antimicrobial composition comprising an effective antimicrobial amount of compound of the formula I as claimed in claim 1 or a physiologically acceptable salt thereof together with a pharmaceutically acceptable carrier.

5. A fungicidal composition comprising an effective fungicidal amount of a compound of the formula I as claimed in claim 1 or a physiologically acceptable salt thereof together with a pharmaceutically acceptable carrier.

6. A method of treating microbes which comprises administering to a host in need of such treatment an effective antimicrobial amount of a compound of the formula I as claimed in claim 1 or a physiologically acceptable salt thereof with or without a pharmaceutically acceptable carrier.

7. A method for treating a fungus in vitro or in vivo which comprises administering to the fungus or to a host in need of treatment an effective fungicidal amount of a compound of the formula I as claimed in claim 1 or a physiologically acceptable salt thereof, with or without a pharmaceutically acceptable carrier.

* * * * *

UNITED STATES PATENT AND TRADEMARK OFFICE
CERTIFICATE OF CORRECTION

PATENT NO. : 4,870,088
DATED : September 26, 1989
INVENTOR(S) : ERNST BLUME et al.

It is certified that error appears in the above-identified patent and that said Letters Patent is hereby corrected as shown below:

Claim 1, column 70, line 47, delete "$C_3-C_8$)" and substitute therefor --$(C_3-C_8)$--;

Claim 1, column 70, line 52, after "is" insert --(1)--; and

Claim 1, column 71, line 20, delete "(Chd 1-$C_4$)" and substitute therefor --$(C_1-C_4)$--.

Signed and Sealed this

Thirtieth Day of April, 1991

Attest:

HARRY F. MANBECK, JR.

*Attesting Officer*  *Commissioner of Patents and Trademarks*